(12) United States Patent
Ho et al.

(10) Patent No.: US 8,490,624 B2
(45) Date of Patent: Jul. 23, 2013

(54) PATIENT INTERFACE WITH VARIABLE FOOTPRINT

(75) Inventors: Peter Chi Fai Ho, Pittsburgh, PA (US); Douglas M. Mechlenburg, Murrysville, PA (US)

(73) Assignee: RIC Investments, LLC, Wilmington, DE (US)

( * ) Notice: Subject to any disclaimer, the term of this patent is extended or adjusted under 35 U.S.C. 154(b) by 894 days.

(21) Appl. No.: 11/937,175

(22) Filed: Nov. 8, 2007

(65) Prior Publication Data

US 2008/0121234 A1 May 29, 2008

Related U.S. Application Data

(60) Provisional application No. 60/858,748, filed on Nov. 13, 2006.

(51) Int. Cl.
*A62B 18/02* (2006.01)

(52) U.S. Cl.
USPC ............ 128/206.24; 128/204.18; 128/205.25; 128/206.21

(58) Field of Classification Search
USPC ............ 128/202.27, 202.25, 206.21, 206.23, 128/206.24, 206.25, 206.26, 206.28, 207.11, 128/207.13
See application file for complete search history.

(56) References Cited

U.S. PATENT DOCUMENTS

| | | | |
|---|---|---|---|
| 6,401,713 B1 * | 6/2002 | Hill et al. ................ | 128/204.21 |
| 6,490,737 B1 | 12/2002 | Mazzei et al. | |
| 6,712,072 B1 | 3/2004 | Lang | |
| 2006/0162729 A1 | 7/2006 | Ging et al. | |
| 2007/0215161 A1 * | 9/2007 | Frater et al. .............. | 128/206.24 |
| 2009/0139527 A1 * | 6/2009 | Ng et al. .................. | 128/206.26 |
| 2009/0199857 A1 * | 8/2009 | Peake et al. .............. | 128/206.28 |

FOREIGN PATENT DOCUMENTS

| | | |
|---|---|---|
| CN | 1623610 A | 6/2005 |
| WO | WO03090827 A1 | 11/2003 |
| WO | WO2005123166 A1 | 12/2005 |
| WO | WO 2006/050559 | 5/2006 |

OTHER PUBLICATIONS

Thorax, "Non-Invasive Ventilation in Acute Respiratory Failure", British Thoracic Society Standards of Care Committee, 2002; vol. 57, pp. 192-211.
Hess, D, "Noninvasive Ventilation in Neuromuscular Disease: Equipment and Application", Respiratory Care, Aug. 2006; vol. 51, No. 8, pp. 896-912.

* cited by examiner

*Primary Examiner* — Justine Yu
*Assistant Examiner* — LaToya M Louis
(74) *Attorney, Agent, or Firm* — Michael W. Haas

(57) ABSTRACT

A system/method for reducing or eliminating application of continuous, repeated, and/or excessive pressure at the contact footprints of a patient interface device and headgear assembly. For example, a patient interface with a plurality of cushions, each producing a different contact footprint when worn by the patient is employed. As another example, a plurality of patient interface devices, each having a cushion that produces a different contact footprint when worn by the patient, are employed. As another example, a patient interface device having a cushion, the configuration/shape of which can be altered such that the contact footprint which it produces is also changed, is employed. The contact footprint to which the patient is exposed is altered after a predetermined time period.

10 Claims, 20 Drawing Sheets

PATIENT INTERFACE WITH VARIABLE FOOTPRINT

CROSS-REFERENCE TO RELATED APPLICATIONS

This application claims priority under 35 U.S.C. §119(e) from provisional U.S. patent application No. 60/858,748 filed Nov. 13, 2006 the contents of which are incorporated herein by reference.

BACKGROUND OF THE INVENTION

1. Field of the Invention

The present invention pertains to patient interface devices and more particularly to eliminating undesirable consequences caused by continuous, repeated, and/or excessive pressure associated with wearing patient interface devices.

2. Description of the Related Art

There are numerous situations where it is necessary or desirable to deliver a flow of breathing gas to the airway of a patient. For example, it is known to deliver a flow of breathing gas to a patient during at least a portion of the breathing cycle to treat breathing and/or cardiac disorders such as obstructive sleep apnea syndrome, chronic obstructive pulmonary disease, congestive heart failure, respiratory distress syndrome, and other breathing and/or cardiac disorders.

Generally, a pressure generating device is employed to produce the flow of breathing gas which is delivered to a patient interface device via a patient conduit. The patient interface device is in fluid communication with, and is structured to deliver the flow of breathing gas to, the airway of the patient.

The patient interface device may be, for example, a nasal mask, full-face mask (i.e., a nasal/oral mask), or a total face mask structured to be placed on and/or over the face of the patient. The patient interface device typically includes a mask cushion and shell. The patient interface device may also include, for example and without limitation, a forehead support, a chin support, and/or a cheek support. Each of these supports may have an associated cushion which comes in contact with the patient's face. A headgear assembly, which typically contacts the back and/or top of the patient's head, may be employed to secure the patient interface device to the patient.

Upon contact with the patient's face, the mask cushion deforms slightly creating a seal between the patient interface device and the patient's face. This seal minimizes leakage of the flow of breathing gas being delivered to the airway of the patient. To insure an adequate seal, a patient undergoes a fitting procedure in which the proper size and style of patient interface device is selected. Generally, the patient wears the selected patient interface device until normal wear and tear necessitates that a replacement device be ordered (e.g., every six months to one year). Most patients receive the same size and style mask as a replacement device.

The cushions (e.g., for the mask and supports) are structured to provide a contact footprint relative to the face of such a patient and the headgear assembly is structured to provide a contact footprint relative to the head of such a patient. The term "contact footprint" refers to the portion of the face/head that is contacted by the cushions/headgear, and the immediate surrounding area, when the patient interface device and/or headgear assembly are being worn by the patient. Pressure exerted on the patient's face is generally localized to the contact footprint associated with the cushions and pressure exerted on the top/back of the patient's head is generally localized to the contact footprint associated with the headgear assembly. Because a patient is generally fitted with a single size/style of patient interface device and headgear assembly, the patient is repeatedly exposed to pressures exerted by the patient interface device and headgear assembly at the same locations (i.e., at the contact footprints associated with the patient interface device and headgear assembly).

Continuous, repeated, and/or excessive pressure applied at a contact footprint may cause undesirable consequences. For example, excessive pressure exerted by the mask cushion may cause a patient's skin to breakdown at the contact footprint associated with that cushion. More serious developmental problems may arise for neonatal, infant, and pediatric patients whose facial and cranial contours are dynamic due to growth of the child. For example, pressure exerted by the mask cushion on neonatal, infant, and pediatric patients may cause facial and bone deformation at or near the contact footprint associated with that cushion.

Accordingly, a need exists for an apparatus and method for providing improved comfort for a patient receiving a flow of breathing gas which overcomes these and other problems associated with known systems.

SUMMARY OF THE INVENTION

In accordance with an aspect of the present invention, a method for delivering a breathing gas to an airway of a patient comprises communicating the breathing gas to the airway of such a patient via a patient interface device structured to produce a contact footprint relative to such patient, and altering the contact footprint relative to such patient after a predetermined time period.

According to another aspect of the present invention, a method for providing a respiratory therapy regimen to a patient, comprises fitting such a patient with a patient interface device, wherein the patient interface device has a cushion structured to produce a first contact footprint relative to the face of such patient and a headgear assembly structured to produce a second contact footprint relative to the head of such patient, delivering a flow of breathing gas to the airway of such patient via the patient interface device, and changing at least one of the first contact footprint and the second contact footprint after a predetermined period by one of (a) altering the shape of the cushion, (b) substituting, for the patient interface device, another patient interface device having a cushion structured to produce a different first contact footprint, (c) substituting, for the cushion, another cushion structured to produce a different first contact footprint, (d) adjusting the headgear assembly to change a pressure distribution about the first contact footprint, (e) adjusting the headgear assembly to change a pressure distribution about the second contact footprint, and (f) substituting, for the headgear assembly, another headgear assembly structured to produce a different second contact footprint.

According to another aspect of the present invention, a patient interface device comprises an adjustable shell, and a cushion coupled with the shell, wherein in response to adjustments to the shell, the cushion is structured to provide multiple contact footprints relative to the face of such a patient.

According to another aspect of the present invention, a patient interface, comprises a shell, and a plurality of interchangeable cushions, wherein each cushion is structured to provide a different contact footprint relative to the face of such a patient According to another aspect of the present invention, a patient interface system comprises a plurality of patient interface devices, each patient interface having a cushion structured to provide a unique contact footprint relative to the face of a patient, wherein at least two of the patient interface devices are alternatingly worn by such a patient.

According to another aspect of the present invention, a system adapted to provide a regimen of respiratory therapy to a patient, comprises a pressure generator structured to produce a flow of breathing gas, a patient interface device structured to communicate the flow of breathing gas to the airway of such a patient, and a patient circuit structured to communicate the flow of breathing gas from the pressure generator to the patient interface device, wherein one of (a) the patient interface device has an adjustable cushion adaptable to provide a plurality of different contact footprints, (b) the patient interface device is selected from a plurality of patient interface devices, each having a cushion structured to provide a different contact footprint, and (c) the patient interface device has a plurality of interchangeable cushions, each cushion structured to provide a different contact footprint, and wherein the contact footprint to which such a patient is exposed is changed after a predetermined period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
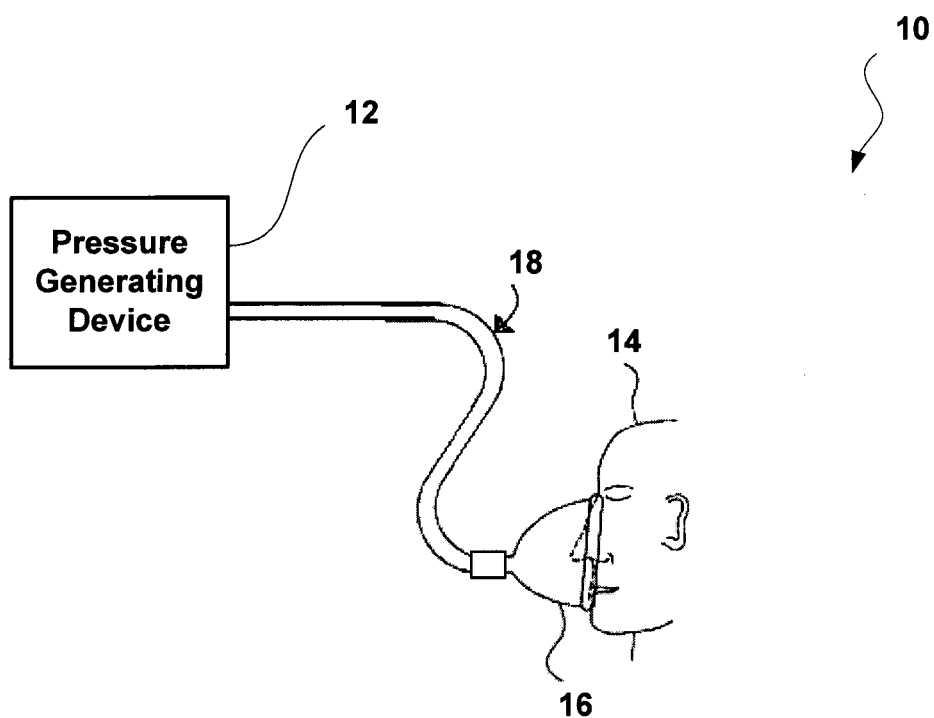
FIG. 1 is a schematic view of a system adapted to provide a regimen of respiratory therapy according to one embodiment of the present invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

As employed herein, the term "contact footprint" refers to a portion of a patient's face and/or head that is contacted by, for example and without limitation, a mask cushion, a forehead support cushion, a chin support cushion, a cheek support cushion, and/or a headgear assembly, and the immediate surrounding area, when the patient interface device and/or headgear assembly are being worn by the patient. Pressure exerted on the patient's face/head by the patient interface device and headgear assembly is generally localized to a contact footprint. Continuous, repeated, and/or excessive pressure applied at a contact footprint may cause undesirable consequences. For example, excessive pressure at the contact footprint associated with a mask cushion may cause a patient's skin to breakdown at the contact footprint. More serious developmental problems may arise for neonatal, infant, and pediatric patients whose facial contours are dynamic due to growth of the child. For example, pressure exerted by the mask cushion on neonatal, infant, and pediatric patients may cause facial and bone deformation.

The present invention is generally directed to systems/methods for reducing or eliminating the application of continuous, repeated, and/or excessive pressure at the contact footprints of the patient interface device and headgear assembly. For example in one embodiment of the present invention, the patient interface device includes a plurality of cushions, each producing a different contact footprint when worn by the patient. A rotation is selected such that a patient does not wear the same cushion for more than the predetermined time period. For example, a first cushion is selected and worn by the patient for a predetermined period. After the predetermined period, a second cushion (producing a different contact footprint when worn by the patient) is substituted for the first cushion and worn for the predetermined period. After the predetermined period, a third cushion is substituted for the second cushion. The first cushion is then substituted for the third cushion after the predetermined period. This rotation is repeated so that the location on the patient's face where pressure is applied by the cushion (i.e., the contact footprint) is continuously changing.

The predetermined period selected may be of any duration which allows the patient interface device and/or headgear assembly to be worn without encountering the undesirable consequences discussed above. In the current example, for instance, a one-day predetermined time period was selected for simplicity; however, it is contemplated that other predetermined periods may be selected while remaining within the scope of the present invention.

Although discussed in context of only three cushions, it is contemplated that any number of cushions may be used. For example in one embodiment, a one-day predetermined time period is selected and seven cushions are used in the rotation. Accordingly, a different cushion is worn by the patient each day of the week. Each cushion may have unique visual markings thereon such as, without limitation, different colors, abbreviations for the day of the week (e.g., M, Tu, We, Th, Fri, Sat, Sun), numbering, etc., so that the patient knows which cushion is to be worn for that specific predetermined period.

As another example, a plurality of patient interface devices, each having a cushion that produces a different contact footprint when worn by the patient, are used to reduce/eliminate the application of continuous, repeated, and excessive pressure in another embodiment of the present invention. As with the previous embodiment, a rotation is selected such that a patient is not exposed to pressure exerted at the same contact footprint for more than the predetermined time period. For example, a first patient interface device is selected and worn by the patient for a predetermined period. After the predetermined period, a second patient interface device (e.g., with a cushion that produces a different contact footprint when worn by the patient) is substituted for the first patient interface device and worn for the predetermined period. After the predetermined period, a third patient interface device is substituted for the second patient interface device. The first patient interface device is then substituted for the third patient interface device after the predetermined period. This rotation is repeated so that the location on the patient's face where pressure is exerted by the patient interface device (i.e., the contact footprint) is continuously changing.

Although discussed in context of only three patient interface devices, it is contemplated that any number of patient interface devices may be used. For example in one embodiment, a one-day predetermined time period is selected and seven patient interfaces are used in the rotation. Accordingly, a different patient interface is worn by the patient each day of the week. Each patient interface device may have unique visual markings thereon such as, without limitation, different colors, abbreviations for the day of the week (e.g., M, Tu, We, Th, Fri, Sat, Sun), numbering, etc.; so that the patient knows which patient interface device is to be worn for that specific predetermined period.

In yet another example, a patient interface device has a cushion, the configuration/shape of which can be altered such that the contact footprint which it produces is also changed. An example of such a patient interface device can be found in U.S. Pat. No. 6,712,072 issued to Lang, the content of which is incorporated herein. Lang discloses a mask base body and a support structure which supports the mask base body. The support structure can repeatedly be deformed plastically above a specific limit temperature so that the respirator mask can be fitted to different facial shapes. It is contemplated that other patient interface devices in which the configuration/shape of the cushion can be altered may be used while remaining within the scope of the present invention.

The configuration/shape of the cushion is altered such that the patient is not exposed to the same contact footprint for more than the predetermined time period. For example, the patient interface device is manipulated such that the cushion produces a first contact footprint relative to the patient. The patient interface device is then worn for a predetermined period by the patient. After the predetermined period, the patient interface device is manipulated such that the cushion produces a second contact footprint. The patient interface device is again worn for the predetermined period. After the predetermined period, the patient interface device is manipulated such that the cushion produces a third contact footprint. The patient interface device is then worn for the predetermined period. This process is repeated so that the location on the patient's face where pressure is exerted by the patient interface device (i.e., the contact footprint) is continuously changing.

Although discussed in context of only three different configurations, it is contemplated that any number of configurations may be used. For example in one embodiment, a one-day predetermined time period is selected and seven configurations are used in the rotation. Accordingly, a different configuration is used for each day of the week.

It is contemplated that the contact footprint produced by any of the patient interface device cushions (e.g., mask cushion; forehead support cushion; chin support cushion; cheek support cushion; etc.) may be altered to reduce/eliminate the undesirable consequences associated with the application of continuous, repeated, and/or excessive pressure at a contact footprint. Furthermore, although the previous examples focused on patient interface devices, it is contemplated (as will be discussed below) that the same systems/methods may be adapted for, or in combination with, a headgear assembly without departing from the scope of the present invention.

A system 10 adapted to provide a regimen of respiratory therapy to a patient 14 according to one embodiment is generally shown in FIG. 1. System 10 includes a pressure generating device 12, a patient circuit 18, and a patient interface device 16. Pressure generating device 12 is structured to generate a flow of breathing gas and may include, without limitation, ventilators, pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support systems.

Patient circuit 18 is structured to communicate the flow of breathing gas from pressure generating device 12 to patient interface device 16. Patient circuit 18 may also be referred to as a patient conduit. Patient interface device 16 may be a nasal mask, a full-face mask, or a total face mask structured to be placed on and/or over a portion of the face of patient 14. Any type of patient interface device 16, however, which facilitates the non-invasive delivery of the flow of breathing gas communicated from pressure generating device 12 to the airway of patient 14 may be used while remaining within the scope of the present invention. As shown in FIG. 1, patient interface device 16 is directly coupled with patient conduit 18; other arrangements, however, are contemplated. Although discussed in conjunction with patient interface devices adapted for non-invasive delivery of the flow of breathing gas, it is contemplated that the present invention may be adapted for patient interface devices adapted for invasive delivery of the flow of breathing gas.

Figure 2:
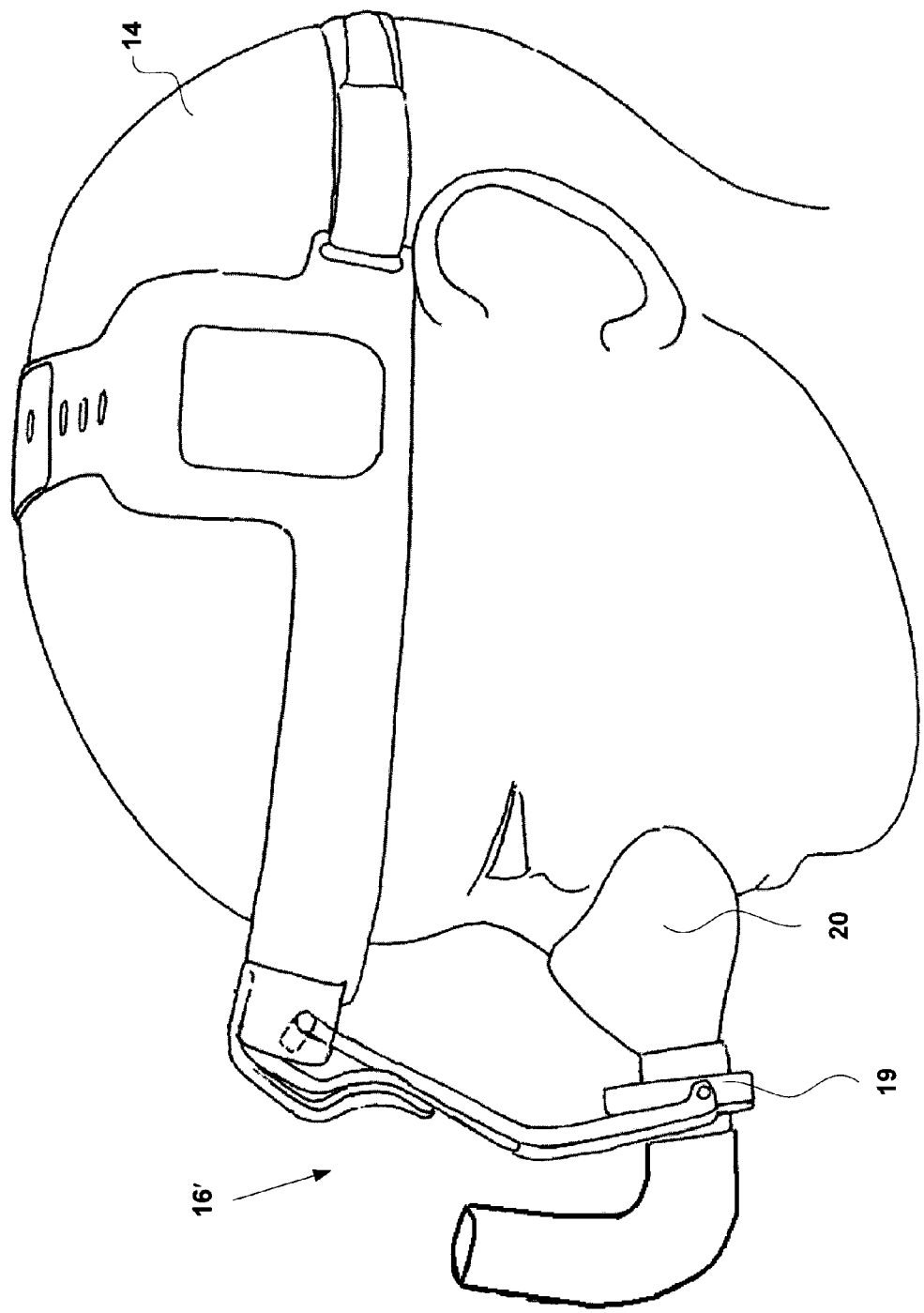
FIG. 2 shows a nasal mask being worn by a patient according to one embodiment of the present invention.

A patient interface device 16' is illustrated in FIG. 2. In the current embodiment, patient interface 16' is a nasal mask (for example, the ComfortLite™ nasal mask manufactured and distributed by Respironics, Inc. of Murrysville, Pa.). Patient interface device 16' generally includes a shell 19 and a plurality of cushions 20 (only one of which is shown in FIG. 2), each of which provides a different contact footprint when in contact with a patient's face. Patient interface 16' is adapted to allow the plurality of cushions 20 to be easily coupled/decoupled from shell 19. Accordingly, a cushion rotation may be established in which a different cushion 20 is worn by patient 14 for each predetermined period.

In the current embodiment, for example, the predetermined period is conveniently set as one day and patient interface device 16' has seven cushions 20 associated therewith; one cushion for each day of the week. Accordingly, a cushion rotation is established wherein a different one of the seven cushions 20 is coupled to shell 19 for each day of the week. As can be seen in FIGS. 3-9, each cushion 20 provides a unique contact footprint when worn by the patient.

Figure 3:
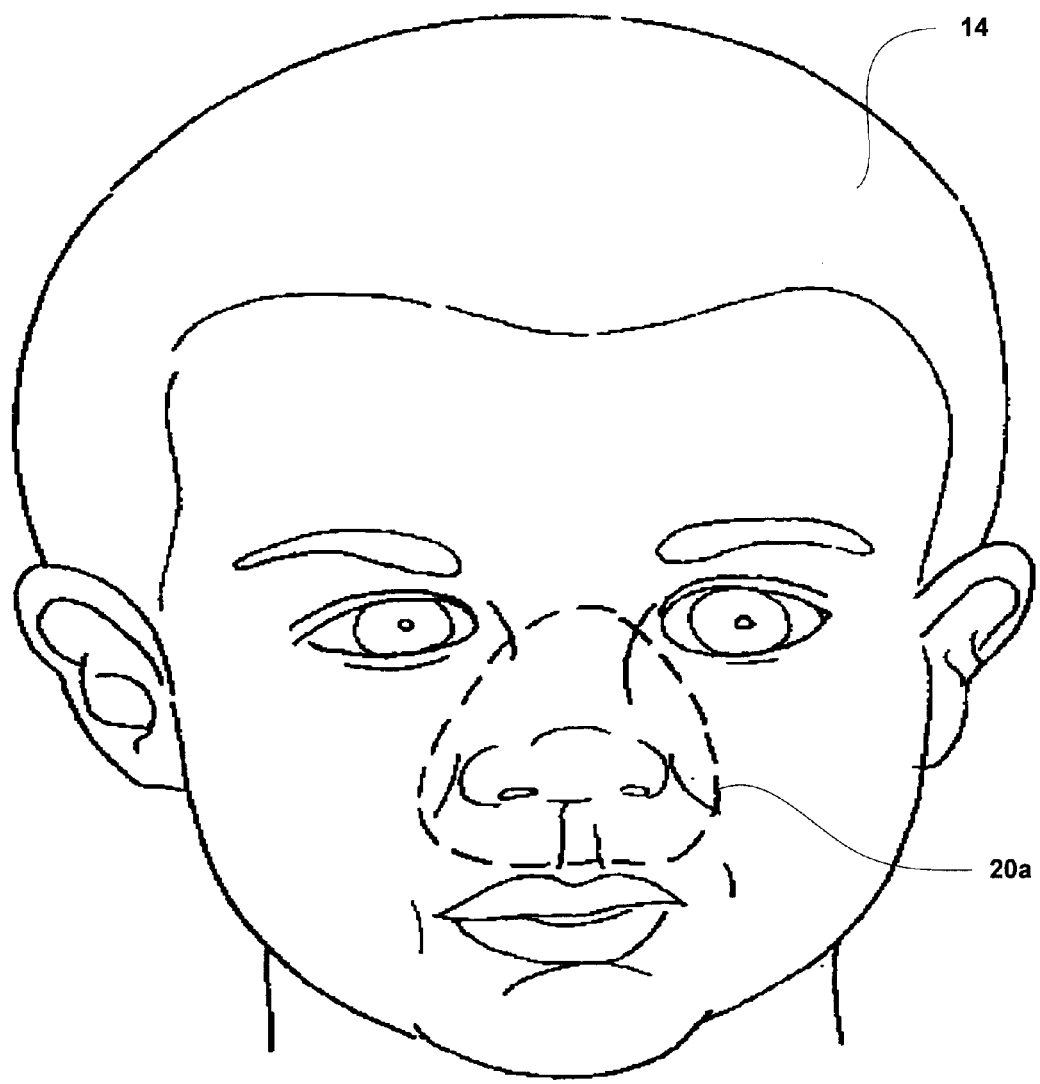
FIGS. 3-9 illustrate various contact footprints for the nasal mask of FIG. 2 according to one embodiment of the present invention.
Figure 4:
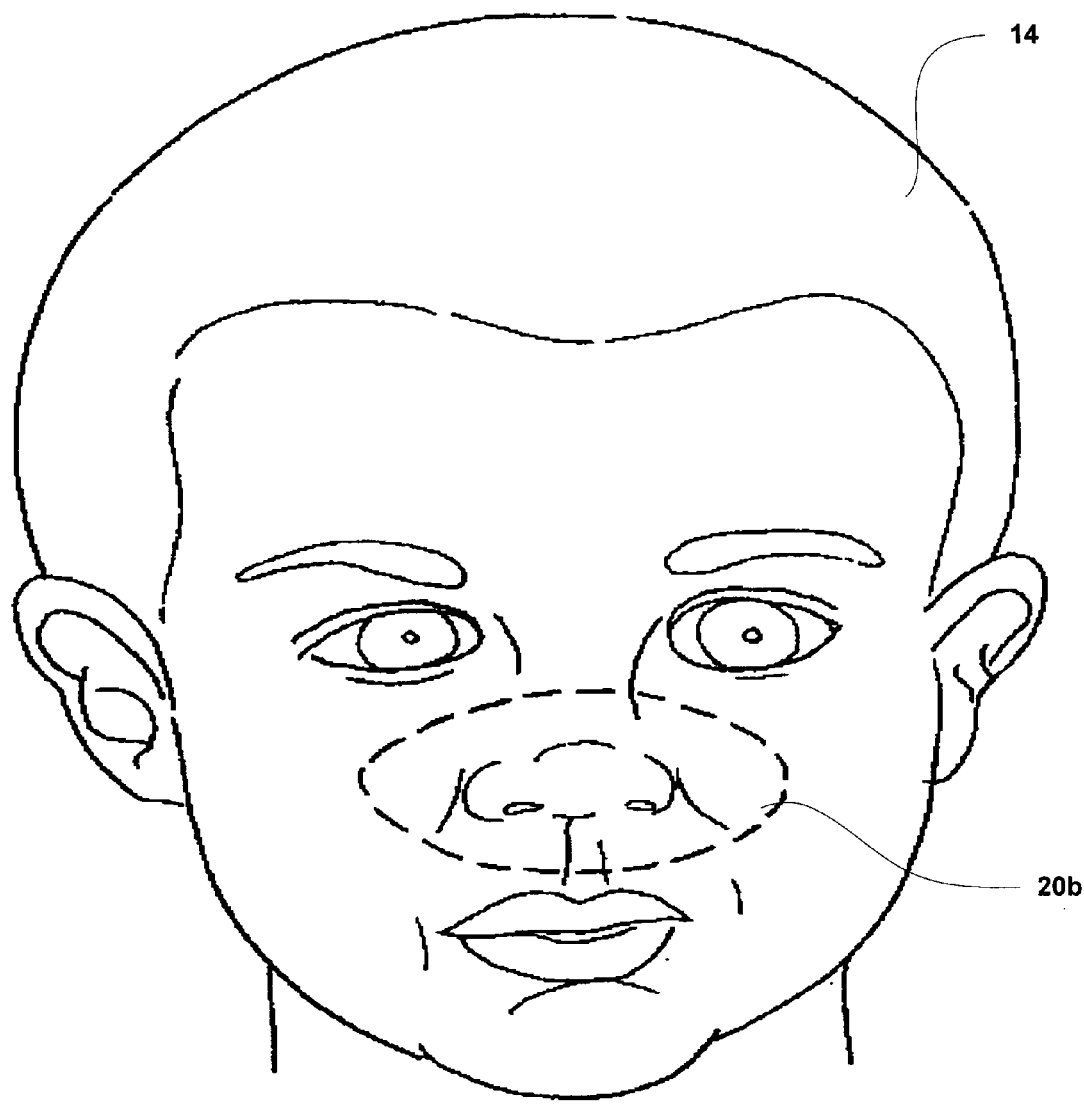
Figure 5:
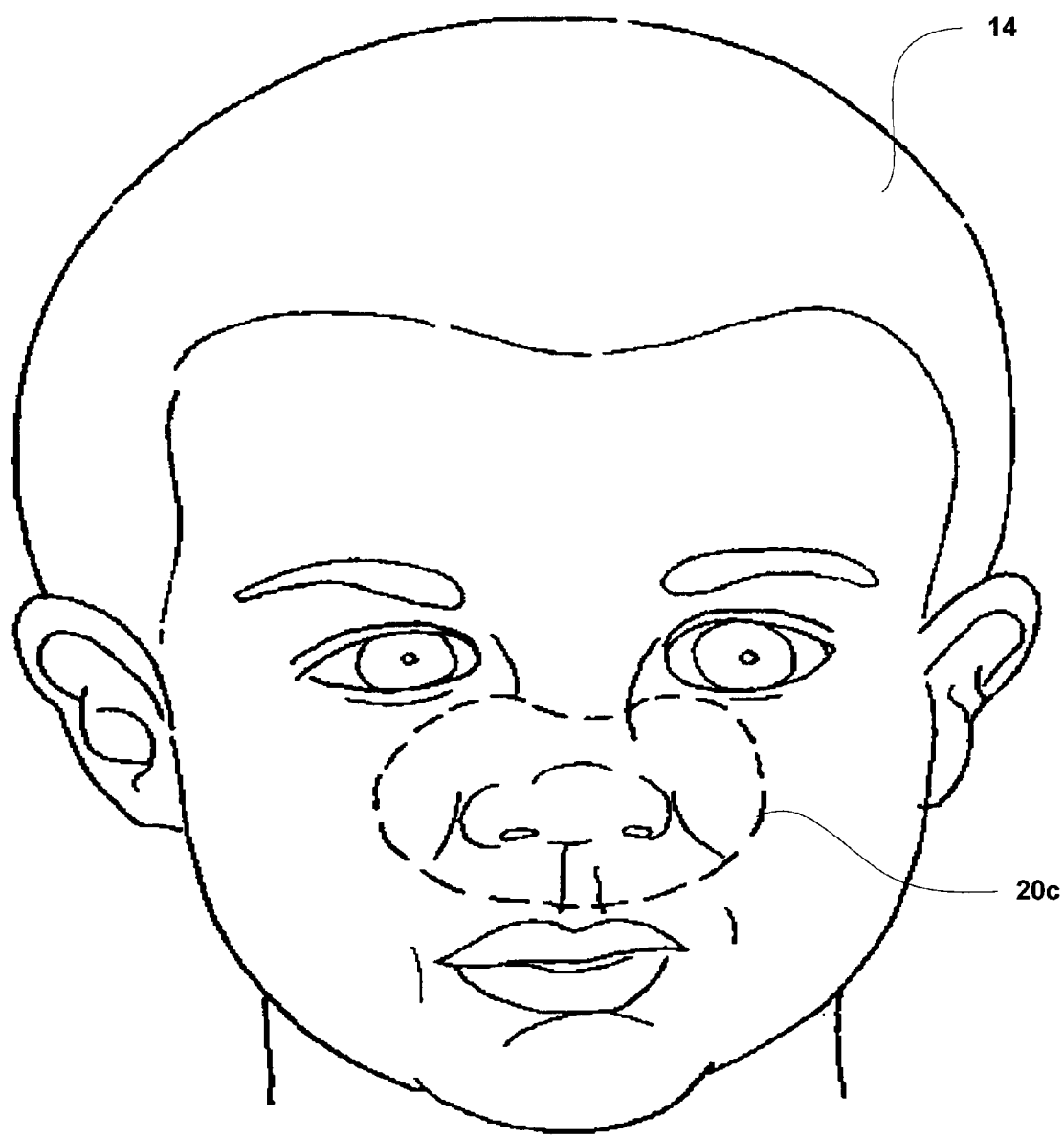
Figure 6:
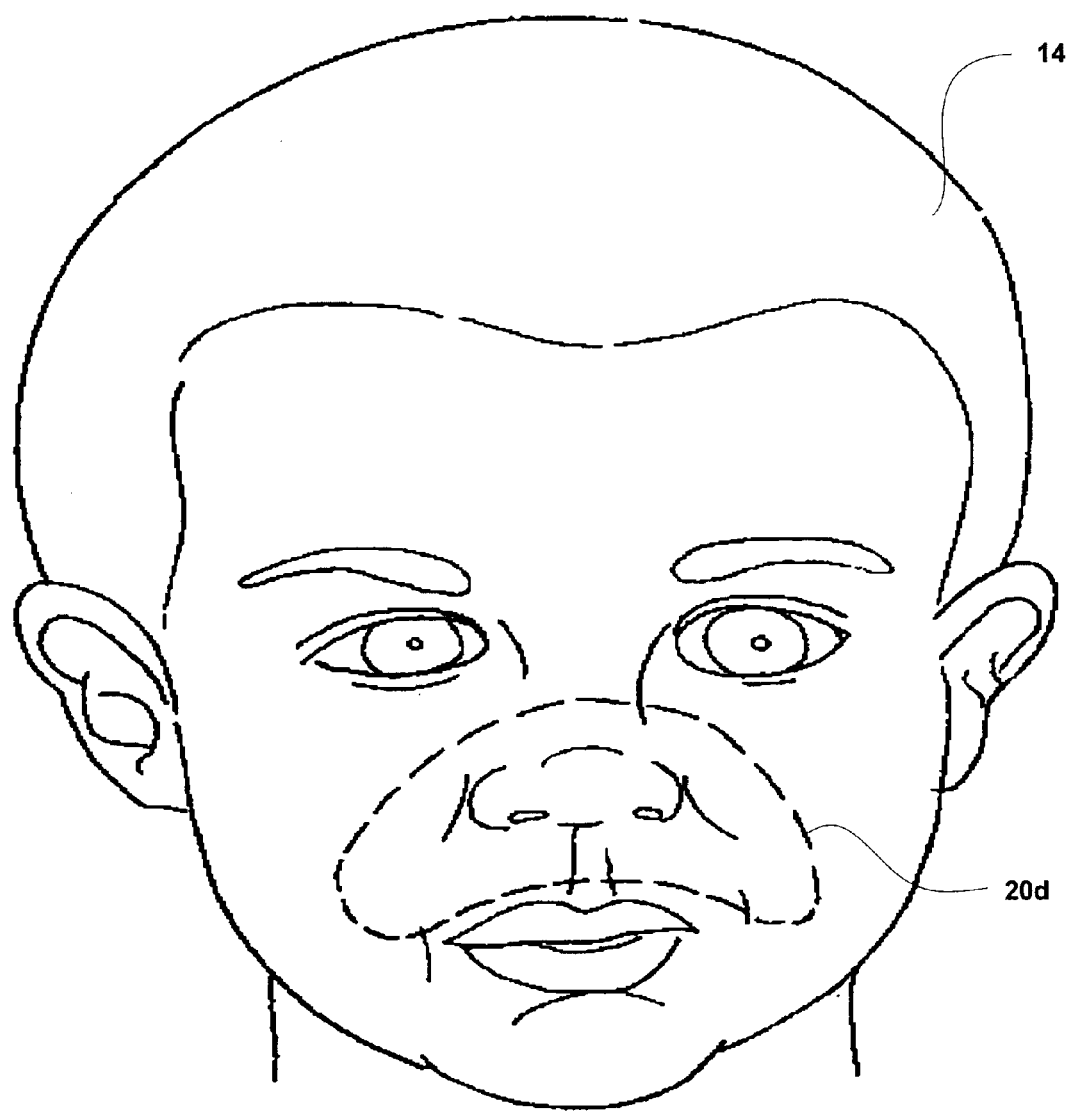
Figure 7:
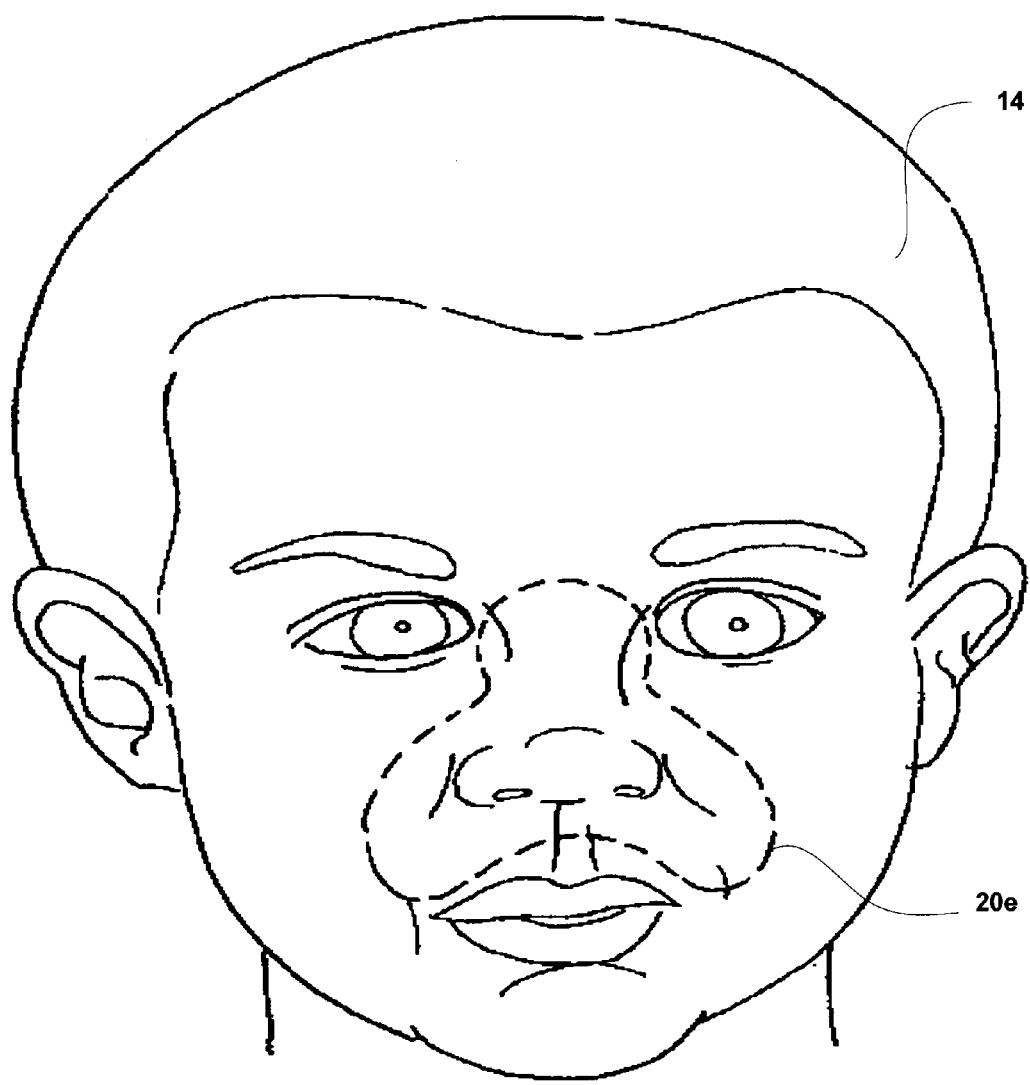
Figure 8:
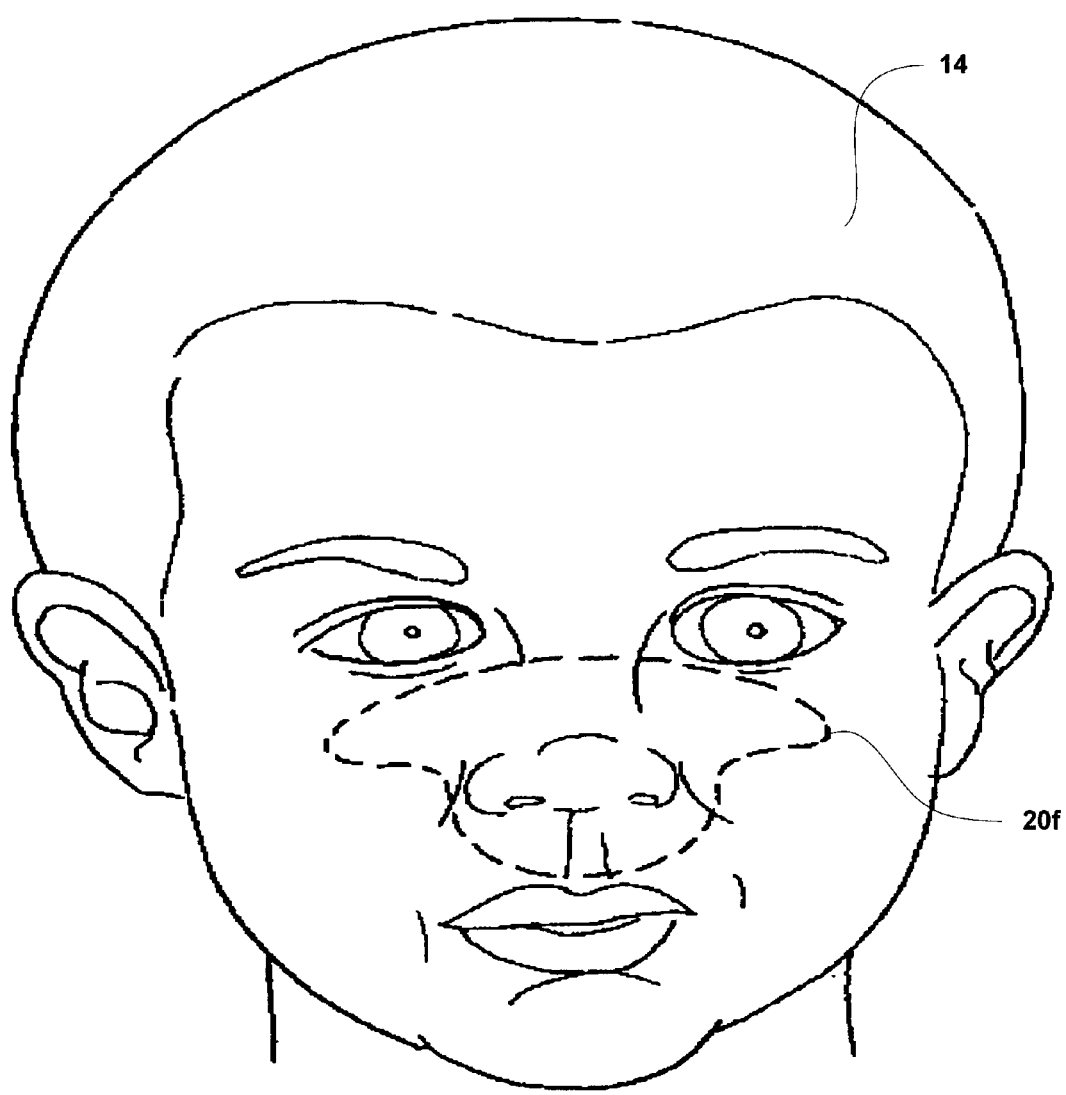
Figure 9:
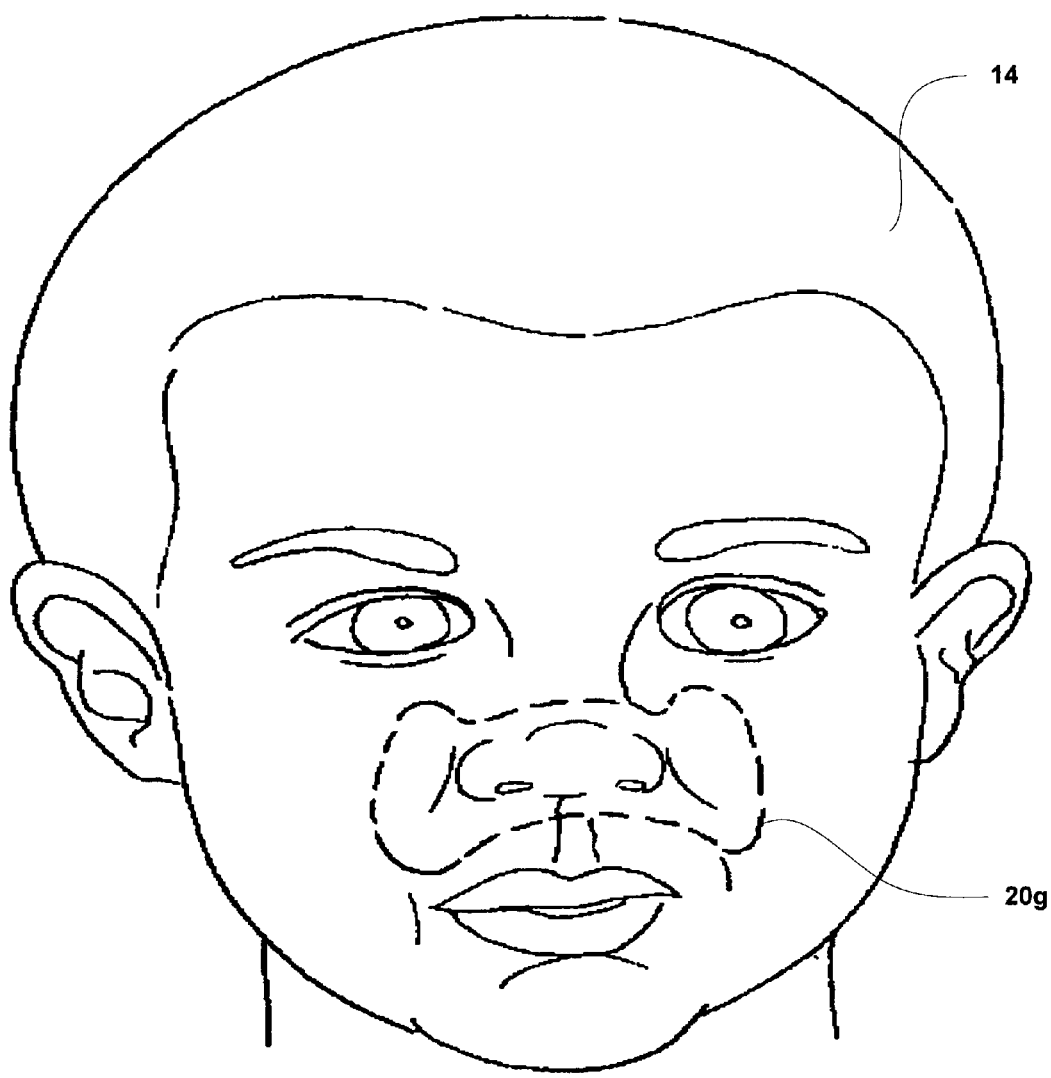

FIG. 3, for instance, shows the contact footprint 20a associated with a first cushion (e.g., a cushion worn on Monday). Contact footprint 20a, which is generally triangular in shape, extends from the nasal bone (e.g., between the eyes of patient 14) to the portion of the face between the upper lip and the nares (i.e., to the philtrum and nasolabial sulcus). In contrast to contact footprint 20a, contact footprint 20b associated with a second cushion (e.g., a cushion worn on Tuesday) shown in FIG. 4 is generally elliptical in shape. Contact footprint 20b extends from a point lower on the patient's 14 nasal bone (e.g., below the eyes) to the portion of the face between the upper lip and the nares (i.e., to the philtrum and nasolabial sulcus). Comparing FIG. 4 to FIG. 3, it is also evident that contact footprint 20b extends to a different portion of the patient's cheekbones.

Referring now to FIGS. 5-9, it can be seen that contact footprints 20c-20g associated with the five other cushions 20 (e.g., cushions worn on Wednesday through Sunday) are different than contact footprints 20a and 20b. Accordingly, by selecting a cushion 20 according to the established rotation, patient 14 is able to prevent the undesirable consequences caused by continuous, repeated, and/or excessive pressure exerted at a single contact footprint.

Although the differences in the contact footprints illustrated in FIGS. 2-9 generally arise from the difference in the shape of the associated cushions, it is contemplated that different contact footprints may arise from substantially similar shaped cushions. For example, cushions having substantially the same shape, but constructed from different materials (e.g., silicon, gel, etc.) and/or having a different arrangement (e.g., double flap, air-filled, dual layer, etc.) may produce different contact footprints.

Furthermore, although FIGS. 2-9 were discussed in conjunction with a patient interface device 16' with a plurality of cushions associated therewith, it should be noted that similar results may be obtained by, for example and without limitation, using a plurality of different patient interface devices (each having a cushion with a different contact footprint) and/or using a patient interface device with a reconfigurable cushion. Additionally, it is contemplated that a different number of cushions/patient interface devices/cushion configurations (two, for example) may be employed while remaining within the scope of the present invention.

Figure 10:
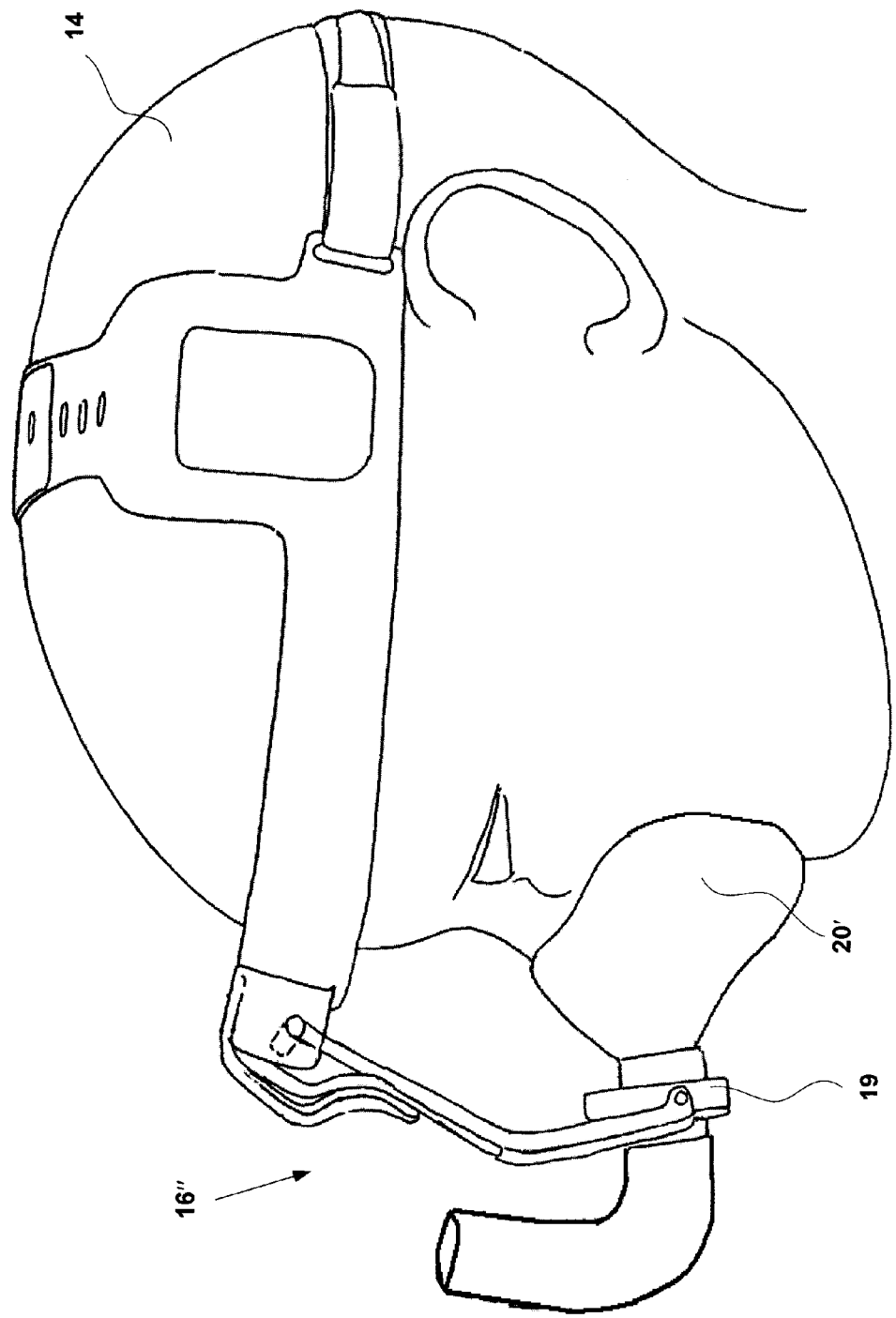
FIG. 10 shows a full-face mask being worn by a patient according to one embodiment of the present invention.

A patient interface 16" according to another embodiment is illustrated in FIG. 10. Patient interface 16" is a full-face mask (i.e., a nasal/oral mask). Patient interface 16" generally includes a shell 19 and a plurality of cushions 20' (only one of which is shown in FIG. 10), each of which provides a different contact footprint when in contact with a patient's face. Patient interface 16" is adapted to allow the plurality of cushions 20' to be easily coupled/de-coupled from shell 19. Accordingly, a rotation may be established in which a different cushion 20' is used for each predetermined period.

Figure 11:
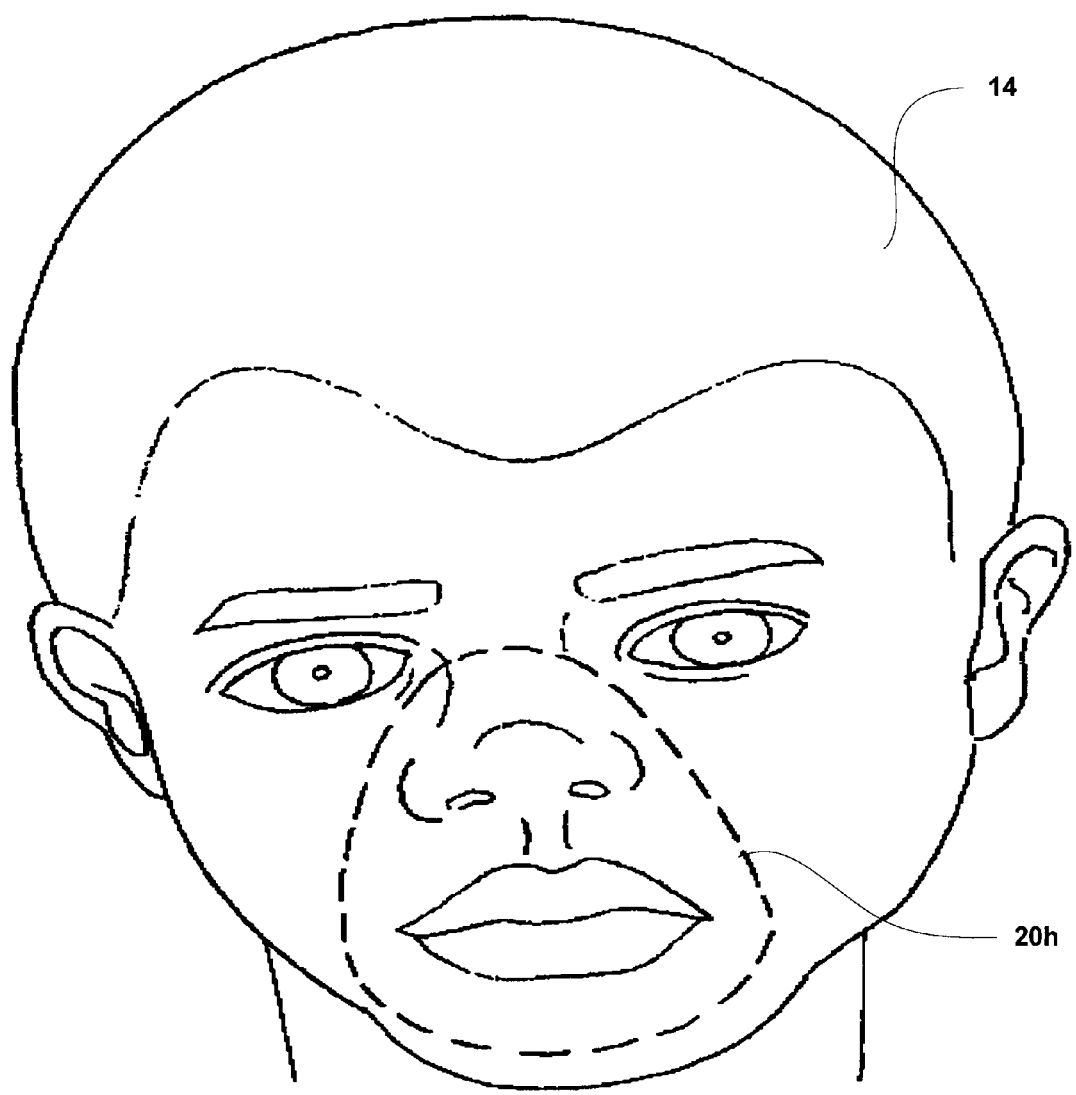
FIGS. 11-13 illustrate contact footprints provided by various full face mask cushions according to one embodiment of the present invention.
Figure 12:
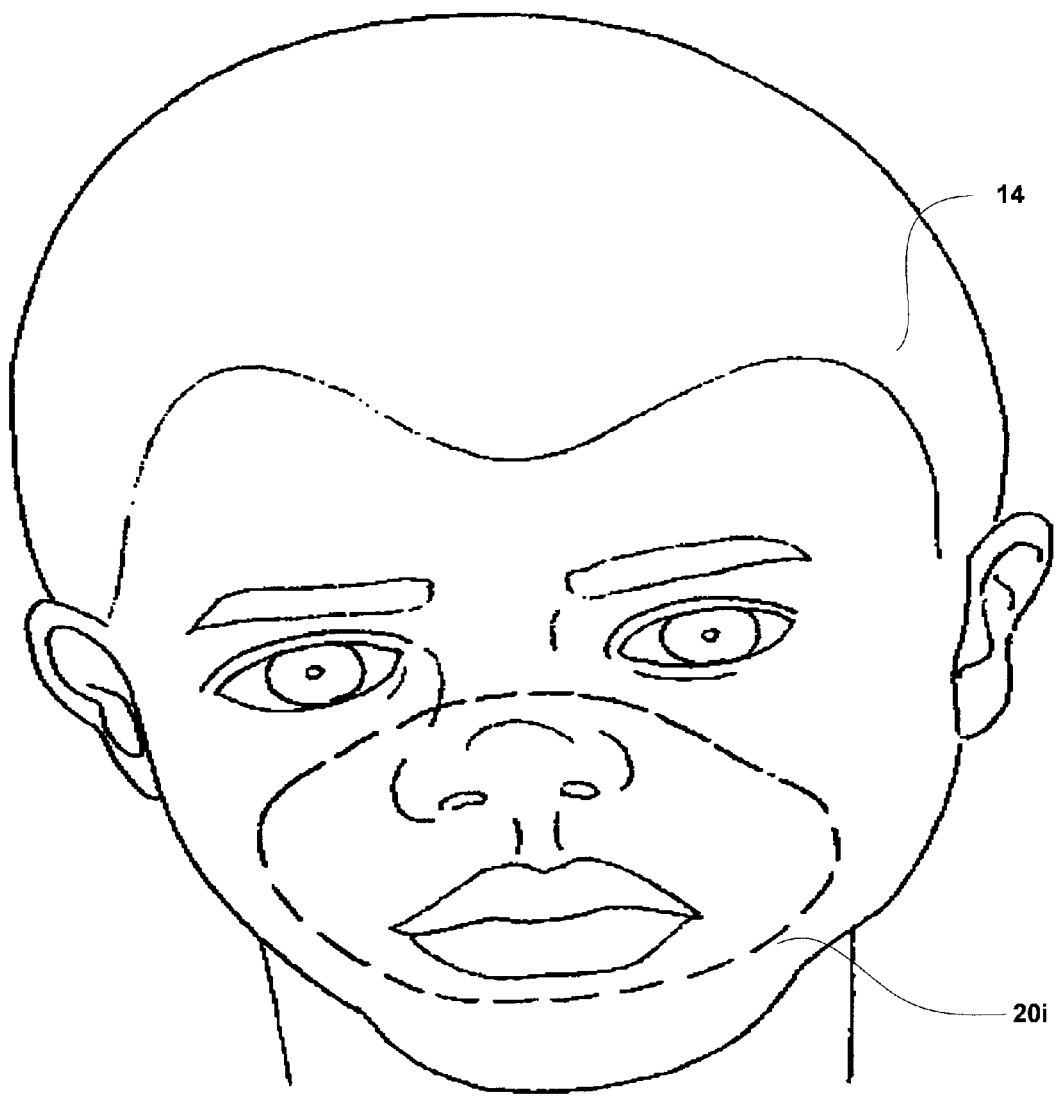
Figure 13:
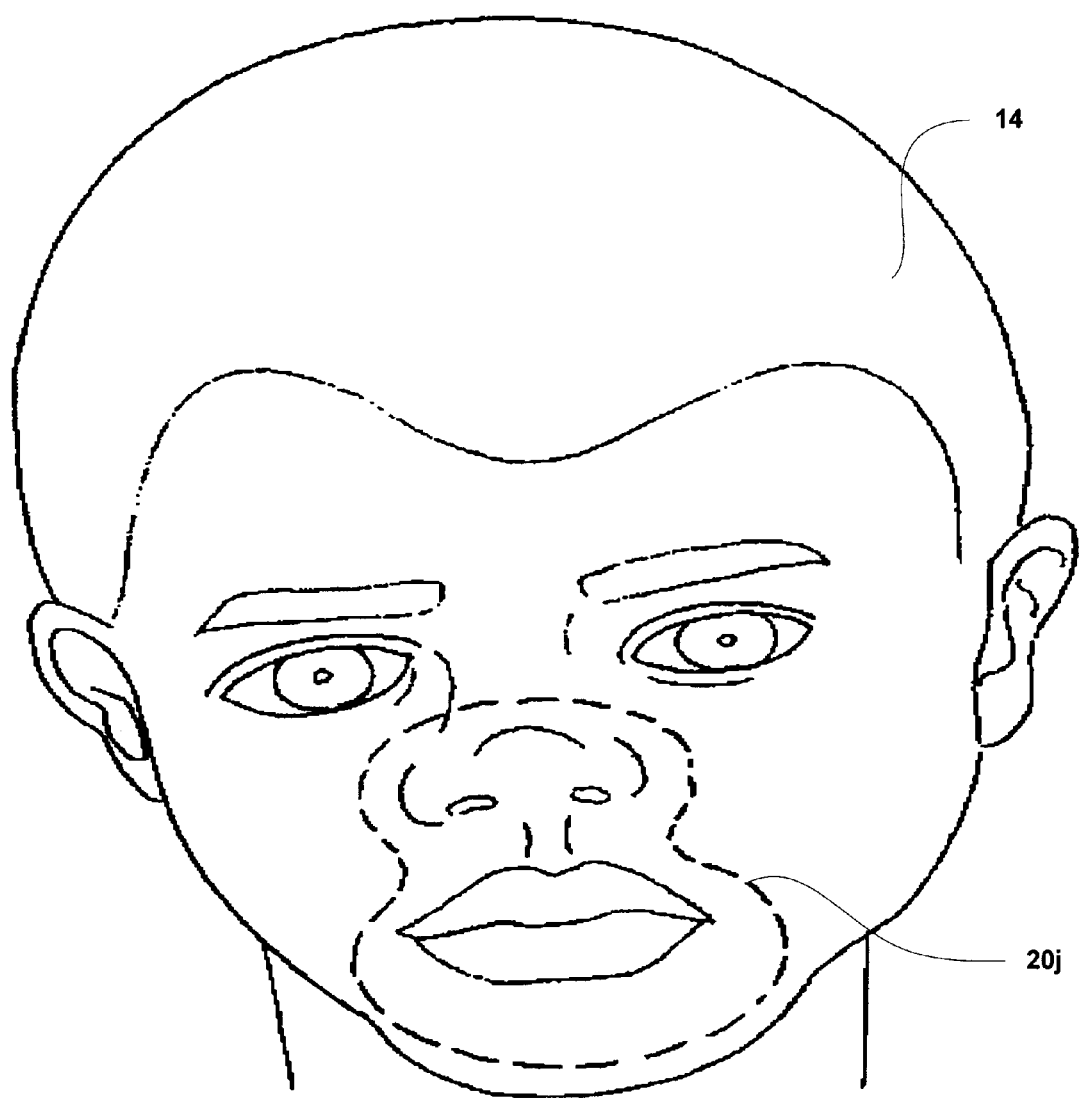

In the current embodiment, for example, patient interface device 16" has three cushions 20' associated therewith, although a different number of cushions may be used while remaining within the scope of the present invention. As discussed above in conjunction with FIGS. 2-9, a cushion rotation is established wherein a different cushion 20' is coupled to shell 19 after a predetermined period, for example, one day. As can be seen in FIGS. 11-13, each cushion 20' provides a unique contact footprint when worn by the patient.

FIG. 11, for instance, shows the contact footprint 20h associated with a first cushion. Contact footprint 20h, which is generally triangular in shape, extends from the nasal bone (e.g., between the eyes of patient 14) to the portion of the face between the lower lip and the mental protuberance. In contrast to contact footprint 20h, contact footprint 20i associated with a second cushion shown in FIG. 12 is generally elliptical in shape. Contact footprint 20i extends from a point lower on the patient's 14 nasal bone (e.g., below the eyes) to the portion of the face between the lower lip and the mental protuberance. Comparing FIG. 12 to FIG. 11, it is also evident that contact footprint 20i extends to a different portion of the patient's cheekbones.

Referring to FIG. 13, the contact footprint 20j associated with a third cushion is shown. Contact footprint 20j, which generally has a "FIG. 8" design, extends from the nasal bone, from a point below the patient's 14 eyes, to the portion of the face between the lower lip and the mental protuberance. Comparing FIG. 13 to FIGS. 11 and 12, it is also evident that contact footprint 20j does not extend as far onto the patient's cheekbones.

Although the differences in the contact footprints illustrated in FIGS. 10-13 generally arise from the difference in the shape of the associated cushions, it is contemplated that different contact footprints may arise from substantially similar shaped cushions. For example, cushions having substantially the same shape, but constructed from different materials (e.g., silicon, gel, etc.) and/or having a different arrangement (e.g., double flap, air-filled, dual layer, etc.) may produce different contact footprints.

Furthermore, although FIGS. 10-13 were discussed in conjunction with a patient interface device 16" with a plurality of cushions associated therewith, it should be noted that similar results may be obtained by, for example and without limitation, using a plurality of different patient interface devices (each having a cushion with a different contact footprint) and/or using a patient interface device with a reconfigurable cushion. Additionally, it is contemplated that a different number of cushions/patient interface devices/cushion configurations (two, for example) may be employed while remaining within the scope of the present invention.

Although the previous examples were generally limited to altering the contact footprint produced by the mask cushion of the patient interface device, it is contemplated that the contact footprint produced by any number of the patient interface device cushions (e.g., mask cushion; forehead support cushion; chin support cushion; cheek support cushion; etc.) may be altered to reduce/eliminate the undesirable consequences associated with the application of continuous, repeated, and/or excessive pressure at a contact footprint. The contact footprint produced by a patient interface having both a mask cushion and a forehead support cushion may be altered, for example and without limitation, by altering the mask cushion, the forehead support cushion, or both the mask cushion and the forehead support cushion.

Figure 14:
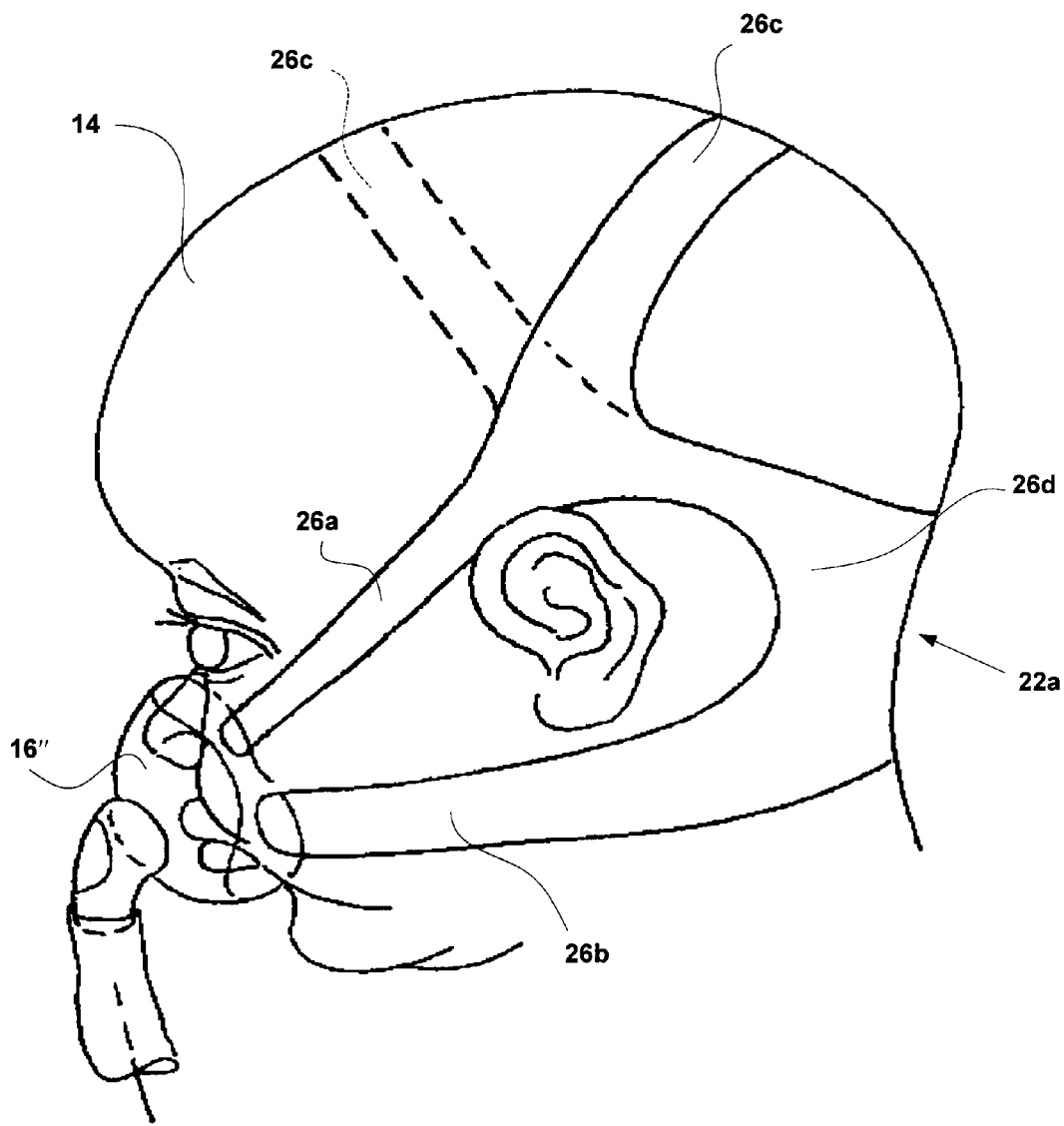
FIGS. 14-17 illustrate various headgear assemblies for use according to an embodiment of the present invention.

A number of headgear assemblies, each with a different contact footprint, are illustrated in FIGS. 14-17. For example, headgear assembly 22a illustrated in FIG. 14 includes an upper connecting strap 26a and lower connecting strap 26b, ends of which couple the headgear assembly 22a to patient interface device 16". The other ends of upper connecting strap 26a and lower connecting strap 26b terminate at a rear joining piece 26d. As seen in FIG. 14, upper connecting strap 26a is worn above the ear; whereas lower connecting strap 26b is worn below the ear. An adjustment strap 26c spans the top of the patient's head. By moving adjustment strap 26c about the top of the patient's head, the contact footprint of headgear assembly 22a may be altered and/or pressure distribution about the contact footprint produced by the mask cushion of patient interface device 16" may be influenced.

Figure 15:
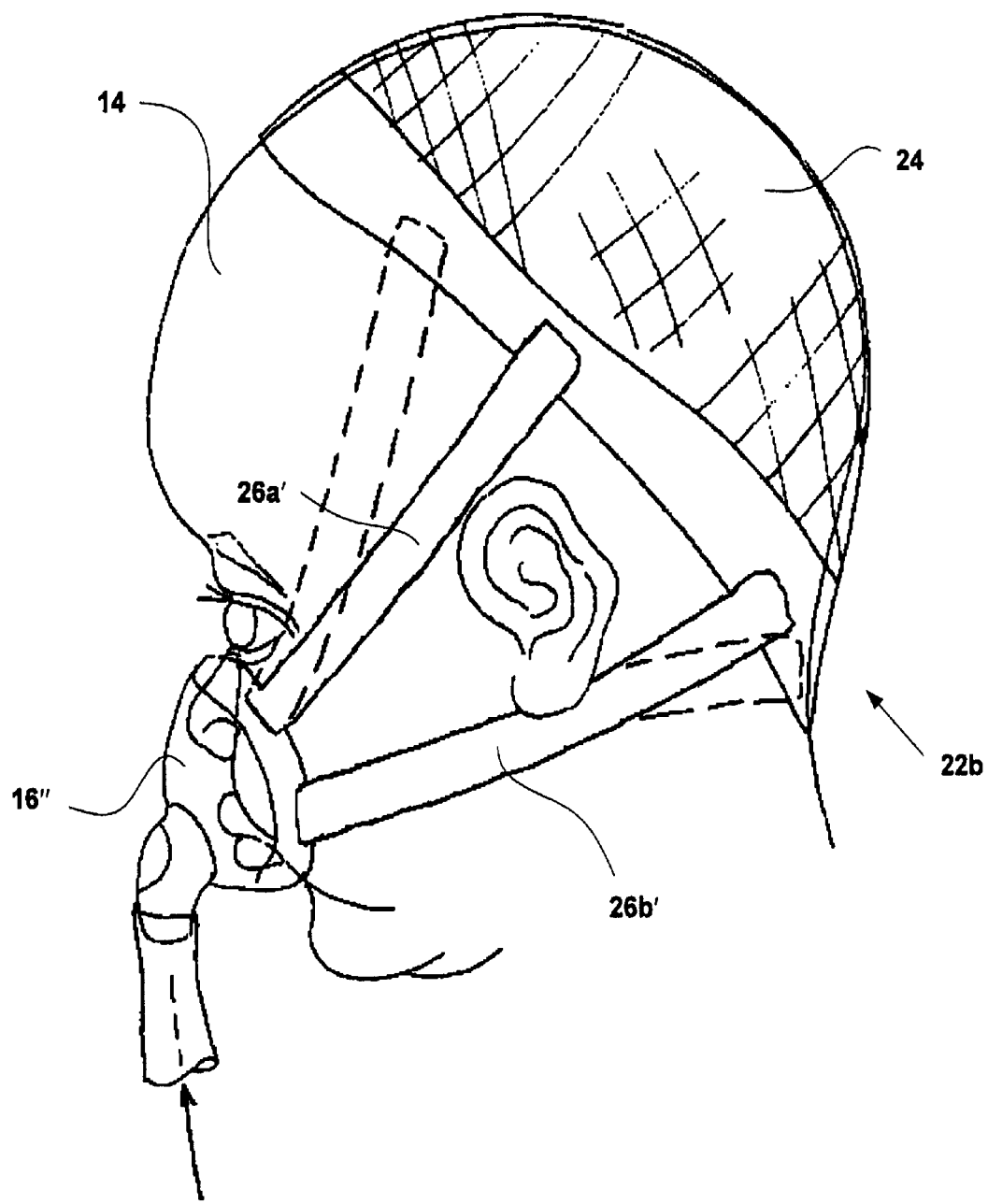

Headgear assembly 22b shown in FIG. 15 includes a mesh headpiece or cap 24 which is structured to rest on the top and back of the patient's head. Headgear assembly 22b also includes an upper connecting strap 26a' and lower connecting strap 26b', first ends of which couple the headgear assembly 22b to patient interface device 16". The other ends of upper connecting strap 26a' and lower connecting strap 26b' are releasably coupled to mesh headpiece 24. In the current embodiment, upper connecting strap 26a' and lower connecting strap 26b' are coupled to mesh headpiece 24 using a hook-and-loop fastener (e.g., VELCRO®). As seen in FIG. 15, upper connecting strap 26a' is worn above the ear; whereas lower connecting strap 26b' is worn below the ear. By moving upper connecting strap 26a' and/or lower connecting strap 26b' about the top of the patient's head, the contact footprint of headgear assembly 22b may be altered and/or pressure distribution about the contact footprint produced by the mask cushion of patient interface device 16" may be influenced.

Figure 16:
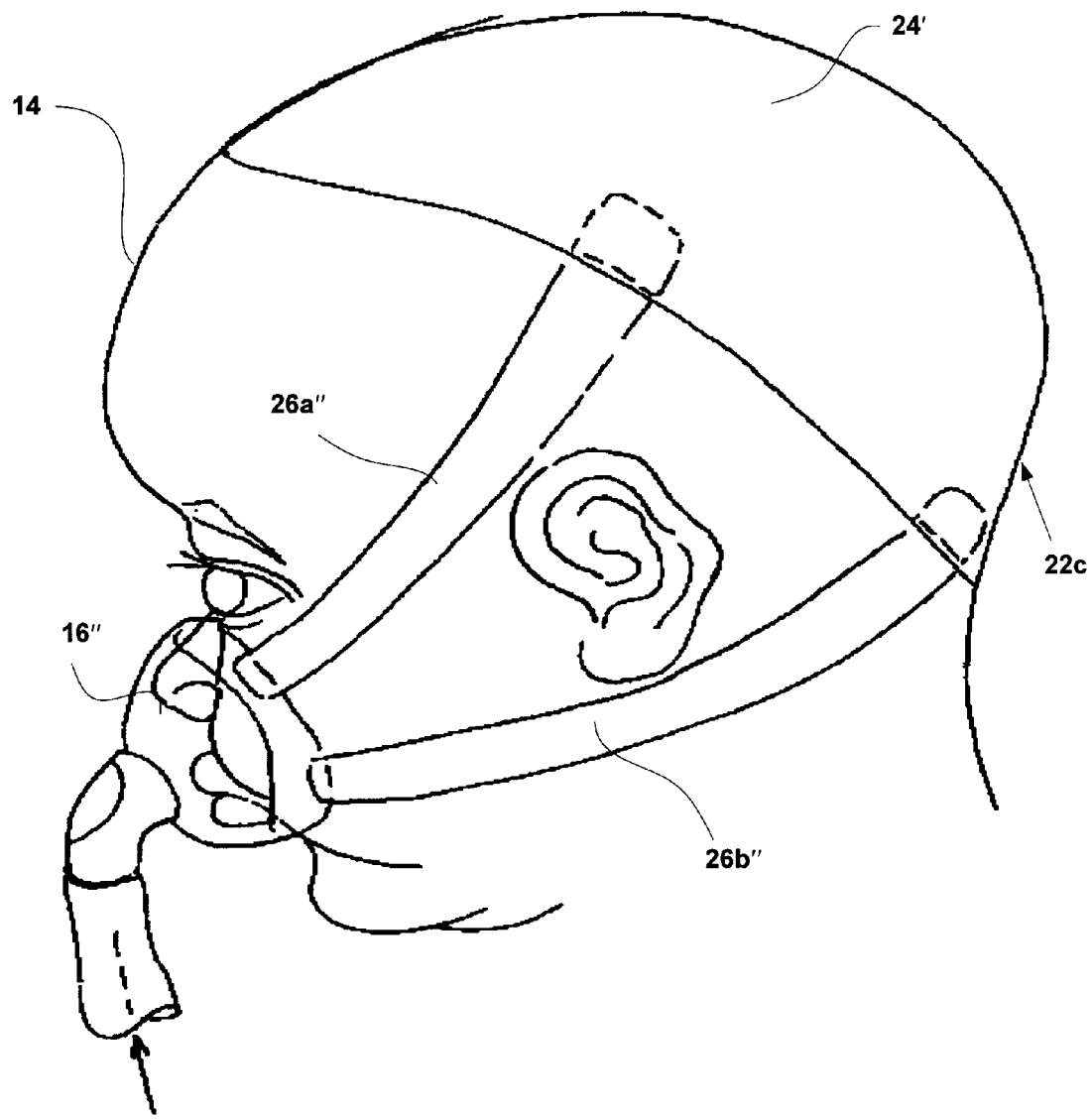

Headgear assembly 22c shown in FIG. 16 is similar to headgear assembly 22b except that the other ends of upper connecting strap 26a" and lower connecting strap 26b" are releasably coupled to a solid headpiece 24' instead of a mesh headpiece 24. By moving upper connecting strap 26a" and/or lower connecting strap 26b" about the top of the patient's head, the contact footprint of headgear assembly 22c may be altered and/or pressure distribution about the contact footprint produced by the mask cushion of patient interface device 16" may be influenced.

Figure 17:
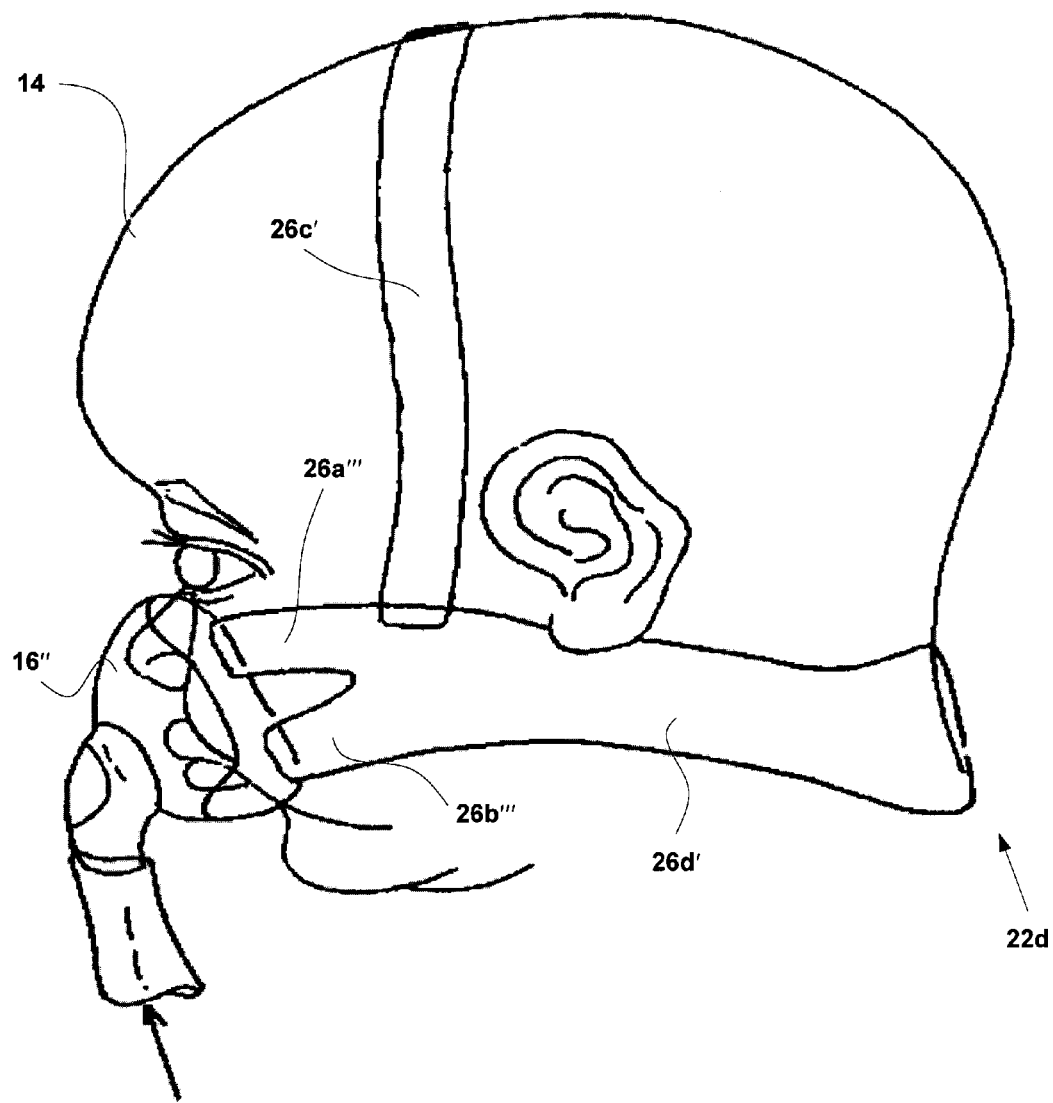
Figure 18:
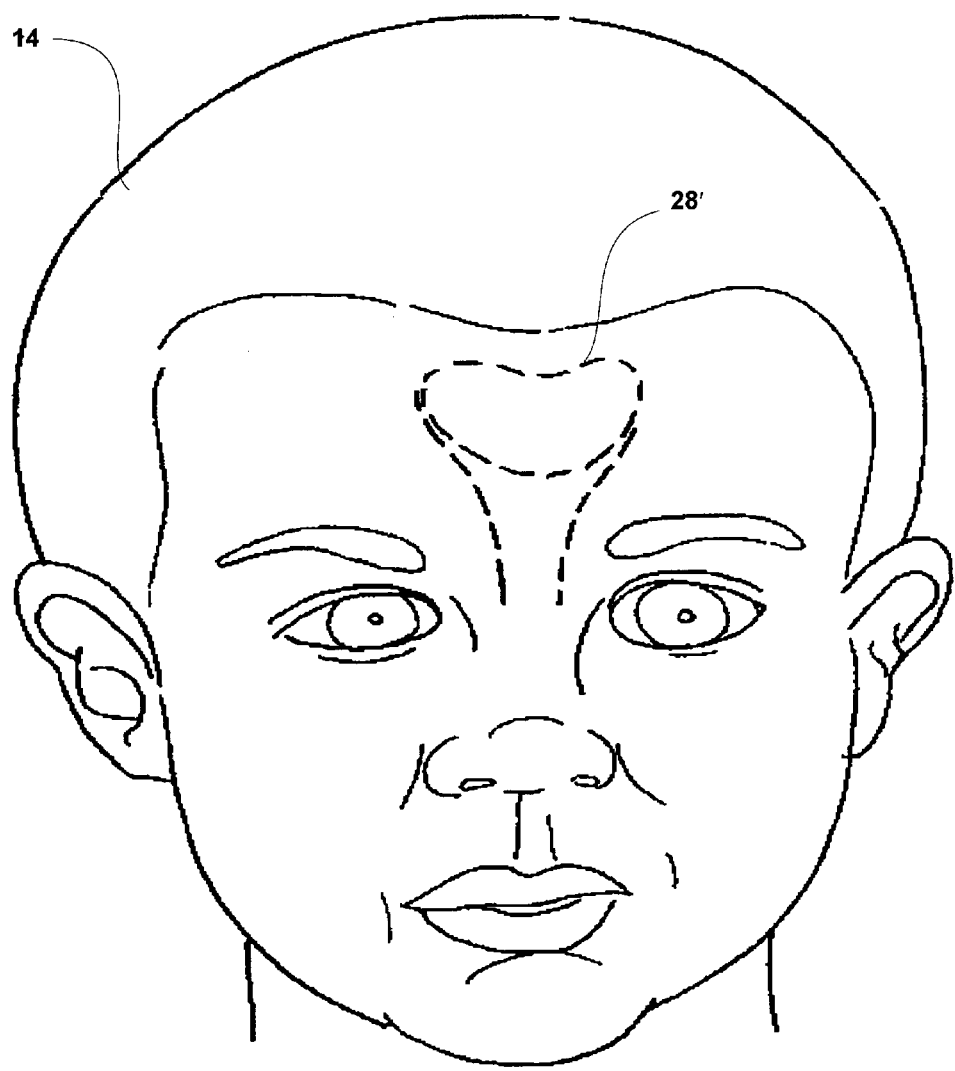
FIGS. 18-20 illustrate contact footprints for various forehead supports according to the principles of the present invention.
Figure 19:
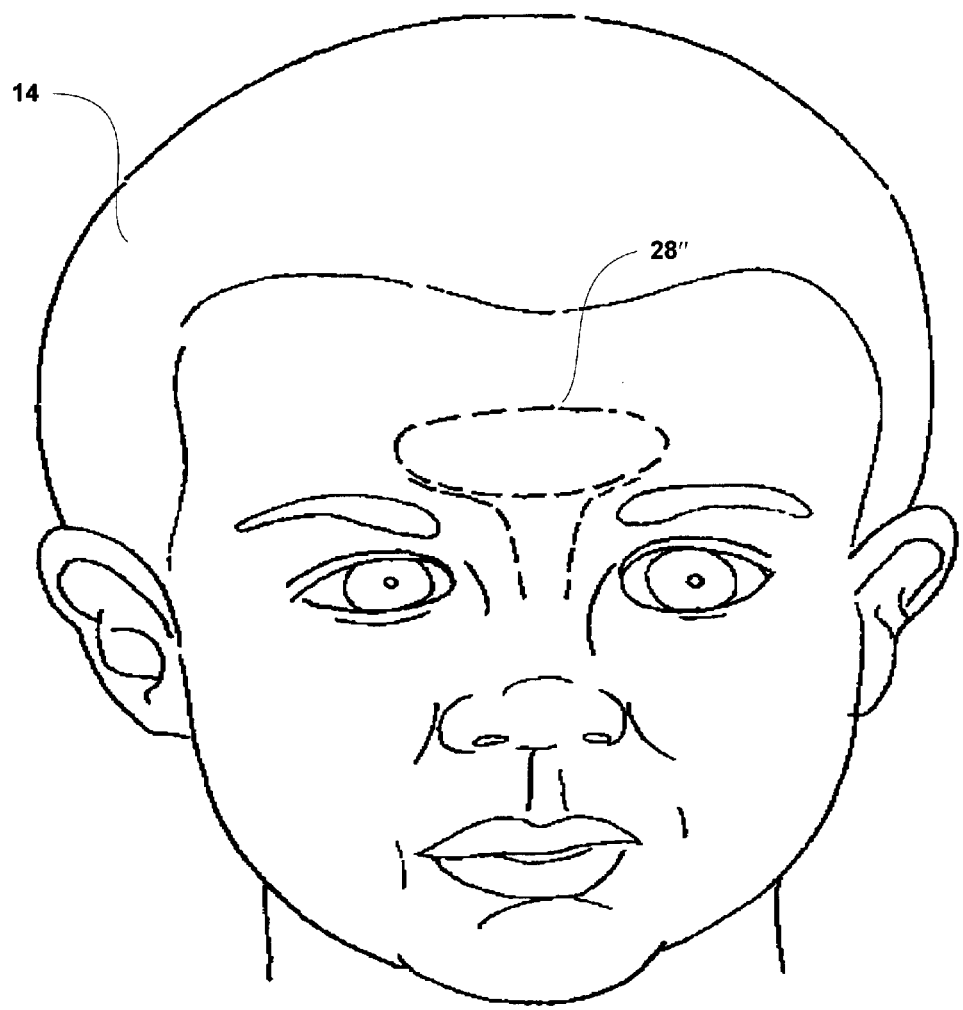
Figure 20:
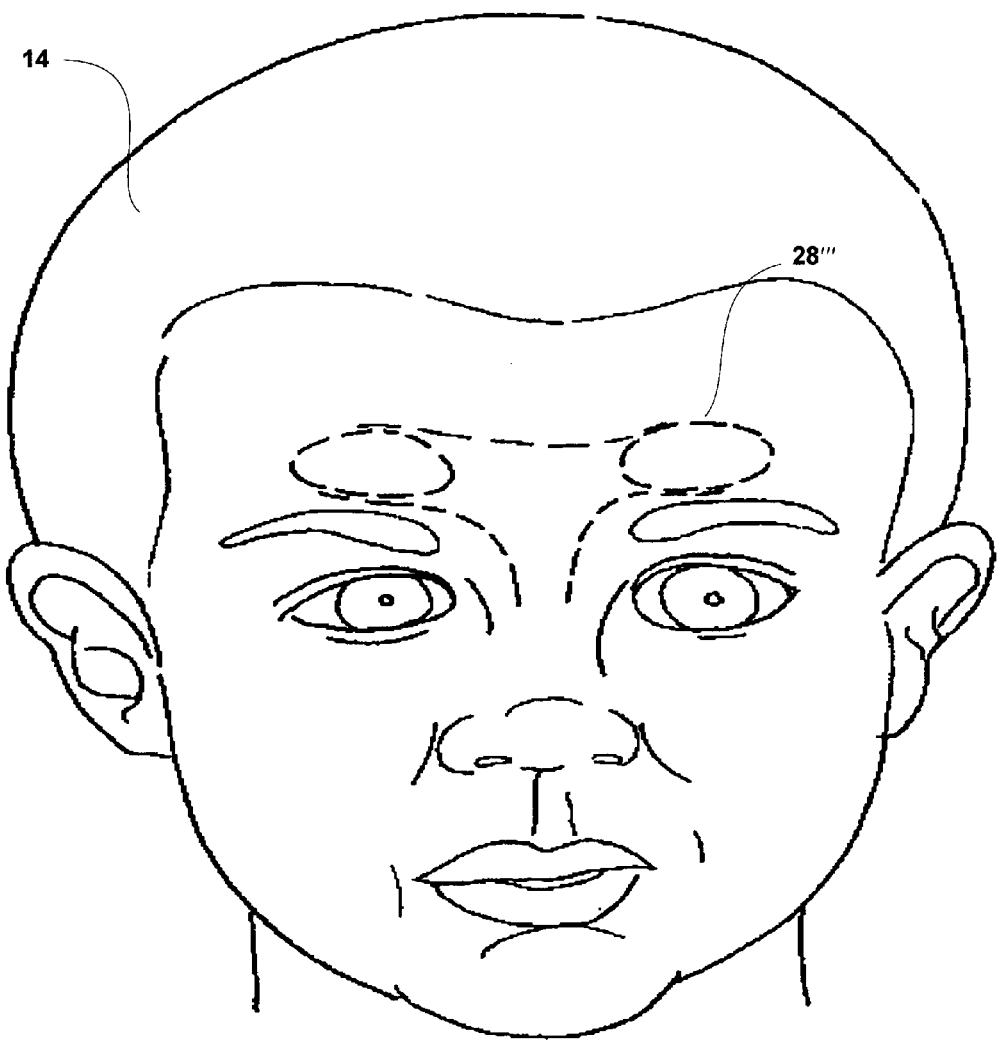

Headgear assembly 22d shown in FIG. 17 includes an upper connecting strap 26a''' and lower connecting strap 26b''', first ends of which couple the headgear assembly 22d to patient interface device 16". The other ends of upper connecting strap 26a''' and lower connecting strap 26b''' terminate at a rear joining piece 26d'. Unlike headgear assembly 22a, upper connecting strap 26a''' and lower connecting strap 26b''' terminate in front of the patient's ear and rear joining piece 26d' is worn below the ear. Headgear assembly 22d also includes an adjustment strap 26c' which is releasably coupled with rear joining piece 26d'. In the current embodiment, adjustment strap 26c' is coupled with rear joining piece 26d' using a hook-and-loop fastener. Adjustment strap 26c' spans the top of the patient's head. By moving adjustment strap 26c' about the top of the patient's head, the contact footprint of headgear assembly 22d may be altered and/or pressure distribution about the contact footprint produced by the mask cushion of patient interface device 16" may be influenced.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method for providing a respiratory therapy regimen to a patient, comprising:
    fitting the patient with a patient interface device, wherein the patient interface device has at least a first cushion, a second cushion and a third cushion associated therewith, wherein the first cushion is structured to produce a first contact footprint relative to the face of the patient by contacting a first portion of the face of the patient, the first contact footprint having a generally triangular shape, wherein the second cushion is structured to produce a second contact footprint relative to the face of the patient by contacting a second portion of the face of the patient, the second contact footprint having a generally elliptical shape, and wherein the third cushion is structured to produce a third contact footprint relative to the face of the patient by contacting a third portion of the face of the patient, the third contact footprint having a third shape, the third shape being different from the generally triangular shape and the generally elliptical, and wherein the patient interface device is selectively configurable to include any one of the first, second and third cushions;
    configuring and using the patient interface device according to a rotation, wherein in the rotation the patient interface device is configured to include the first cushion and a flow of breathing gas is delivered to the airway of the patient via the patient interface device during a first predetermined period, the patient interface device is configured to include the second cushion and a flow of breathing gas is delivered to the airway of the patient via the patient interface device during a second predetermined period, and the patient interface device is configured to include the third cushion and a flow of breathing gas is delivered to the airway of the patient via the patient interface device during a third predetermined period, wherein the first cushion includes a first visual marking indicating the first predetermined period, the second cushion includes a second visual marking indicating the second predetermined period, and the third cushion includes a third visual marking indicating the third predetermined period; and
    after the configuring and using the patient interface device according to the rotation is completed, re-configuring and re-using the patient interface device one or more additional times according to the rotation to deliver a flow of breathing gas to the airway of the patient such that a location on the patient's face wherein pressure is applied by the patient interface device is continuously changing during the respiratory therapy regimen.

2. The method of claim 1, wherein the first cushion, the second cushion and the third cushion comprises one of a mask cushion, a forehead support cushion, a chin support cushion, and a cheek support cushion.

3. The method of claim 1, wherein the patient interface device comprises one of a nasal mask, a full-face mask, and a total face mask.

4. The method of claim 1, wherein the patient interface device has at least a fourth cushion, a fifth cushion, a sixth cushion and a seventh cushion associated therewith, wherein during the rotation the patient interface device is configured to include each of the fourth, fifth, sixth and seventh cushions.

5. The method of claim 4, wherein each of the first, second, third, fourth, fifth, sixth and seventh cushion has a day of the week associated therewith, wherein the first visual marking indicates the day of the week associated with the first cushion, wherein the second visual marking indicates the day of the week associated with the second cushion, wherein the third visual marking indicates the day of the week associated with the third cushion, and wherein the fourth, fifth, sixth and seventh cushions each includes a visual marking indicating that day of the week associated therewith.

6. The method of claim 1, wherein the first, second and third predetermined periods are each a day.

7. A method for providing a respiratory therapy regimen to a patient, comprising:
    fitting the patient with at least first, second and third patient interface devices, wherein the first patient interface device has a first cushion, the second patient interface device has a second cushion and the third patient interface device has a third cushion, wherein the first cushion is structured to produce a first contact footprint relative to the face of the patient by contacting a first portion of the face of the patient, the first contact footprint having a generally triangular shape, wherein the second cushion is structured to produce a second contact footprint relative to the face of the patient by contacting a second portion of the face of the patient, the second contact footprint having a generally elliptical shape, and wherein the third cushion is structured to produce a third contact footprint relative to the face of the patient by contacting a third portion of the face of the patient, the third contact footprint having a third shape different from the generally triangular shape and the generally elliptical shape;

using the first, second and third patient interface devices according to a rotation, wherein in the rotation the first patient interface device is used to deliver a flow of breathing gas to the airway of the patient during a first predetermined period, the second patient interface device is used to deliver a flow of breathing gas to the airway of the patient during a second predetermined period, and the third patient interface device is used to deliver a flow of breathing gas to the airway of the patient during a third predetermined period, wherein the first patient interface device includes a first visual marking indicating the first predetermined period, the second patient interface device includes a second visual marking indicating the second predetermined period, and the third patient interface device includes a third visual marking indicating the third predetermined period; and after the using the first, second and third patient interface devices according to the rotation is completed, re-using the first, second and third patient interface devices according to the rotation one or more additional times to deliver a flow of breathing gas to the airway of the patient such that a location on the patient's face wherein pressure is applied is continuously changing during the respiratory therapy regimen.

8. The method of claim 7, wherein the first, second a third cushions each comprise one of a mask cushion, a forehead support cushion, a chin support cushion, and a cheek support cushion.

9. The method of claim 7, wherein the first, second a third patient interface devices each comprise one of a nasal mask, a full-face mask, and a total face mask.

10. The method of claim 7, wherein the first, second and third predetermined periods are each a day.

* * * * *